(12) United States Patent
Gewolb et al.

(10) Patent No.: US 8,568,336 B2
(45) Date of Patent: Oct. 29, 2013

(54) NON-INVASIVE DEVICE FOR DIAGNOSING GASTROESOPHAGEAL REFLUX

(75) Inventors: Ira H. Gewolb, East Lansing, MI (US); Frank L. Vice, Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 57 days.

(21) Appl. No.: 13/003,986

(22) PCT Filed: Aug. 18, 2009

(86) PCT No.: PCT/US2009/004701
§ 371 (c)(1),
(2), (4) Date: Jun. 2, 2011

(87) PCT Pub. No.: WO2010/021690
PCT Pub. Date: Feb. 25, 2010

(65) Prior Publication Data
US 2011/0313320 A1  Dec. 22, 2011

Related U.S. Application Data

(60) Provisional application No. 61/089,661, filed on Aug. 18, 2008, provisional application No. 61/095,154, filed on Sep. 8, 2008.

(51) Int. Cl.
*A61B 6/00* (2006.01)
(52) U.S. Cl.
USPC ............ 600/586; 600/300; 600/301; 600/593
(58) Field of Classification Search
USPC ................. 600/300, 301, 586, 593
See application file for complete search history.

(56) References Cited

U.S. PATENT DOCUMENTS

| | | | | |
|---|---|---|---|---|
| 4,331,156 A * | 5/1982 | Apple et al. | | 600/501 |
| 4,409,986 A * | 10/1983 | Apple et al. | | 600/528 |
| 5,058,600 A | 10/1991 | Schechter et al. | | |
| 5,159,932 A * | 11/1992 | Zanetti et al. | | 600/508 |
| 5,213,108 A * | 5/1993 | Bredesen et al. | | 600/528 |
| 5,876,350 A | 3/1999 | Lo et al. | | |
| 5,989,193 A * | 11/1999 | Sullivan | | 600/534 |
| 6,050,950 A * | 4/2000 | Mohler | | 600/485 |
| 6,097,984 A | 8/2000 | Douglas | | |
| 6,152,879 A * | 11/2000 | Mohler | | 600/485 |
| 6,179,783 B1 * | 1/2001 | Mohler | | 600/485 |
| 6,416,483 B1 | 7/2002 | Halleck et al. | | |
| 6,478,744 B2 * | 11/2002 | Mohler | | 600/485 |
| 6,537,233 B1 * | 3/2003 | Rangayyan et al. | | 600/586 |
| 7,066,894 B2 | 6/2006 | Halleck et al. | | |

(Continued)

OTHER PUBLICATIONS

"Canadian Application Serial No. 2,729,840—Office Action Received", 1 pg.

(Continued)

*Primary Examiner* — Sean Dougherty
(74) *Attorney, Agent, or Firm* — Schwegman, Lundberg & Woessner, P.A.

(57) ABSTRACT

The present invention provides compositions and methods useful in the diagnosis and management of Gastroesophageal Reflux. Specifically, the inventions provide a device and methods of using the device for accurately, quantitatively, and non-invasively diagnosing Gastroesophageal reflux disease (GERD) in both patients at risk for GERD and patients demonstrating reflux-like symptoms. In particular, the inventions relate to detecting and analyzing upward esophageal movements in patients, such as human infants, children, and adults.

15 Claims, 9 Drawing Sheets

(56) References Cited

U.S. PATENT DOCUMENTS

| | | | |
|---|---|---|---|
| 7,416,531 B2* | 8/2008 | Mohler | 600/528 |
| 7,527,597 B2* | 5/2009 | Sandler et al. | 600/504 |
| 7,702,394 B2* | 4/2010 | Imran | 607/40 |
| 8,265,291 B2* | 9/2012 | Bridger et al. | 381/67 |
| 2001/0039383 A1* | 11/2001 | Mohler | 600/485 |
| 2002/0156398 A1* | 10/2002 | Mansy et al. | 600/586 |
| 2003/0028088 A1* | 2/2003 | Castell et al. | 600/350 |
| 2005/0065450 A1* | 3/2005 | Stuebe et al. | 600/547 |
| 2005/0075583 A1* | 4/2005 | Sullivan | 600/586 |
| 2006/0064037 A1* | 3/2006 | Shalon et al. | 600/586 |
| 2006/0264730 A1* | 11/2006 | Stivoric et al. | 600/390 |
| 2007/0165872 A1* | 7/2007 | Bridger et al. | 381/67 |
| 2007/0208233 A1* | 9/2007 | Kovacs | 600/300 |
| 2008/0183090 A1* | 7/2008 | Farringdon et al. | 600/509 |
| 2008/0269646 A1* | 10/2008 | Chau et al. | 600/595 |
| 2008/0287817 A1* | 11/2008 | Stivoric et al. | 600/508 |
| 2009/0012433 A1* | 1/2009 | Fernstrom et al. | 600/593 |
| 2009/0036790 A1* | 2/2009 | Landesberg et al. | 600/529 |
| 2010/0056956 A1* | 3/2010 | Dufresne et al. | 600/586 |
| 2010/0172839 A1* | 7/2010 | Walker | 424/9.1 |

OTHER PUBLICATIONS

"International Application Serial No. PCT/US2009/004701, International Preliminary Report on Patentability mailed Feb. 22, 2011", 5 pgs.

"International Application Serial No. PCT/US2009/004701, International Search Report mailed Apr. 21, 2010", 4 pgs.

"International Application Serial No. PCT/US2009/004701, Written Opinion mailed Apr. 21, 2010", 4 pgs.

"United Kingdom Application Serial No. 1100291.2, Office Action mailed Sep. 25, 2012", 3 pgs.

"United Kingdom Application Serial No. 1100291.2, Response filed Nov. 30, 2012 to Office Action mailed Sep. 25, 2012", 64 pgs.

Reynolds, E. W., et al., "Variability of Swallow-associated Sounds in Adults and Infants", Dysphagia, 24, (2009), 13-19.

Torrence, C., et al., "A Practical Guide to Wavelet Analysis", Bulletin of the American Meteorological Society, 79(1), (1998), 61-78.

* cited by examiner

NON-INVASIVE DEVICE FOR DIAGNOSING GASTROESOPHAGEAL REFLUX

RELATED APPLICATIONS

This patent application is a U.S. National Stage Application under 35 U.S.C. §371 of PCT/US2009/004701, filed Aug. 18, 2009, and published on Feb. 25, 2010 as WO 2010/021690, which claims the benefit of priority of U.S. Provisional Patent Application Ser. No. 61/095,154, filed on Sep. 8, 2008 and of U.S. Provisional Patent Application Ser. No. 61/089,661, filed on Aug. 18, 2008, which are hereby incorporated by reference herein in their entirety.

FIELD OF THE INVENTION

The present invention provides compositions and methods useful in the diagnosis and management of Gastroesophageal Reflux. Specifically, the inventions provide a device and methods of using the device for accurately, quantitatively, and non-invasively diagnosing Gastroesophageal reflux disease (GERD) in both patients at risk for GERD and patients demonstrating reflux-like symptoms. In particular, the inventions relate to detecting and analyzing upward esophageal movements in patients, such as human infants, children, and adults.

BACKGROUND OF THE INVENTION

Gastroesophageal reflux disease (GERD) is estimated to occur in approximately 50% of normal term infants at the age of 2 months; however approximately 1% still have reflux at one year of age. Reflux is exacerbated in preterm infants, since gastric movements, such as motility and emptying, are lower so that reflux and related symptoms are not as easy to detect. Indeed, many symptoms currently considered to be GERD-related (e.g., apnea) are likely not causally related.

The majority of current efforts to treat GERD in infants involve antacids and increasing gut motility. However, few properly designed prospective studies, at least in infants, have shown efficacy of these treatments. Indeed, antacid treatment in preterm infants may promote adverse overgrowth of bacteria and predispose them to the development of necrotizing enterocolitis.

Similarly in adults, a putative diagnosis of GERD leads to (at least initial) empirical treatment with proton pump inhibitors, which treat the acidity of the refluxate, but not with medications designed to increase gut motility or suppress reflux. Further, because non-acid reflux is difficult to detect and has few if any effective treatments, non-acid reflux is generally ignored in the therapy of adult reflux. Use of an impedance monitor to detect non-acid reflux has been proposed as a new gold standard in the diagnosis and treatment of adult reflux, but significant problems remain with this diagnostic modality (vide infra).

Lower esophageal sphincter (LES) tone is historically considered to be involved in GERD and a focus of treatment. However, resting LES tone is not maturity related since resting LES at all ages exceeds intragastric pressure. Further, LES pressure does not correlate with GERD symptoms additionally making LES related treatments less than optimal.

Currently, the pH probe is the "gold standard" for the detection of reflux symptoms and diagnosis of acid reflux. However, in addition to being an invasive device, where the probe must be internalized in order to contact acid gastric materials, reflux has both acidic and non-acid occurrences, especially in preterm infants. Thus because a pH probe does not accurately measure non-acidic reflux this "gold standard" fails to detect non-acidic reflux. Therefore there is a lack of capability of detecting reflux in a non-invasive manner as well as a greater lack of capability for measuring non-acid reflux. Detection of non-acid reflux is especially important in preterm infants whose stomach acidity is less than in older children and adults.

In conclusion there is a lack of a diagnostic tool for detecting both acidic and non-acidic reflux symptoms for use in detecting reflux and for diagnosing GERD in order to begin providing effective reflux treatments for patients of any age.

SUMMARY OF THE INVENTION

The present invention provides compositions and methods useful in the diagnosis and management of Gastroesophageal Reflux. Specifically, the inventions provide a device and methods of using the device for accurately, quantitatively, and non-invasively diagnosing Gastroesophageal reflux disease (GERD) in both patients at risk for GERD and patients demonstrating reflux-like symptoms. In particular, the inventions relate to detecting and analyzing upward esophageal movements in patients, such as human infants, children, and adults.

The present invention relates to compositions and methods of detecting reflux events, in particular for human subjects. Thus, in one embodiment, the present invention contemplates a system for detecting an esophageal movement in a subject, comprising a low frequency sensor, and more preferably, a very low frequency sensor, wherein said sensor is capable of capturing a sub-audible signal. In a preferred embodiment, the system does not include a device that would capture background noise preventing the visualization of a low frequency reflux associated signal. In another preferred embodiment, the device not included in the system comprises an analog recorder device, such as a microphone and the like. In one embodiment, the system comprises a plurality of sensors e.g. two, three, and four sensors, or more. In one embodiment, the low frequency sensor is an accelerometer capable of capturing a signal ranging between 0 and 100 Hertz. In one embodiment, the low frequency sensor is an accelerometer capable of capturing an acoustical signal below 60 Hertz and above 0 Hertz. In a preferred embodiment, the low frequency sensor is an accelerometer capable of capturing a signal below 40 Hertz and above 0 Hertz. In one embodiment, the sub-audible signal ranges in frequency between 0.1 and 40 Hertz. In one embodiment, the system further comprises a means for removing a signal at 60 Hertz. In one embodiment the means includes but is not limited to a digital stop band filter to remove a signal at 60 Hertz. In a preferred embodiment, the signal is originating from the area of the lower esophageal sphincter of a subject. In one embodiment, the system further comprises a device for converting the sub-audible signal into a digital signal (the sensor or sensors being in electronic communication with said device). In one embodiment, the device includes but is not limited to a sensor capable of analog to digital conversion, an analog to digital converter device, and the like. In one embodiment, the system further comprises software capable of transforming a signal by a conversion algorithm selected from the group consisting of a fast Fourier Transform (FFT) and Continuous Wavelet Transform (CWT). In one embodiment, the system further comprises software capable of capturing a variable selected from the group consisting of frequency, range, amplitude, and duration in time. In one embodiment, the system further comprises software capable of signal pre-amplification and sending the pre-amplified signal to an analog-to-digital signal converter. In one embodiment, the sample rate ranges from 200-300 samples per second. In a further embodiment, the sample rate is 250 samples per second. In one embodiment, the sample signals are for recording as a time signal. In one embodiment, the system further comprises software capable of capturing a variable selected from the group consisting of frequency, range, amplitude, and duration in time. In one embodiment, the system further comprises software capable of visually displaying a signal in a graphical output comprising amplitude, time, and frequency. In one embodiment, the system further comprises software capable of visually displaying a signal in a graphical output comprising millivolts, minutes, and Hertz. In one embodiment, time is displayed in units of any one of seconds, minutes, and hours. In one embodiment, the system further comprises software capable of visually displaying a signal in a graphical output comprising decibels, minutes, and Hertz, wherein said software is in operable combination with a computer processor. In one embodiment, the system further comprises software capable of visually displaying a signal in a graphical output comprising millivolts, minutes, and Hertz, wherein said software is in operable combination with a computer processor. In one embodiment, the system further comprises software capable of distinguishing a reflux event from a non-reflux event, wherein said software is in operable combination with a computer processor. In one embodiment, the system further comprises software capable of real time data analysis, wherein said software is in operable combination with a computer processor. In one embodiment, the system further comprises software capable of diagnosing a reflux disease, wherein said software is in operable combination with a computer processor.

In one embodiment, the present invention contemplates software capable of distinguishing a reflux associated event from a non-reflux associated event, wherein said software is in operable combination with a computer processor. In one embodiment, the present invention contemplates software capable of real time data analysis, wherein said software is in operable combination with a computer processor. In one embodiment, the present invention contemplates a software package comprising software capable of distinguishing a reflux associated event from a non-reflux associated event, software capable of real time data analysis, software capable of diagnosing a reflux disease, and the like, wherein said software is in operable combination with a computer processor.

In one embodiment, the present invention provides a system for identifying an esophageal movement in a subject, comprising, a very low frequency sensor, wherein said sensor is capable of capturing a sub-audible signal, a step amplifier in electronic communication with said sensor, a recorder amplifier, wherein said recorder amplifier is capable of data storage and is in electronic communication with said step amplifier, a computer processor, wherein said processor is capable of data input and formatting and is in electronic communication with said recorder amplifier, and a graphical output of said computer processor, wherein said system does not include an analog recording device. In one embodiment, said sub-audible signal ranges between 1 and 40 Hertz. In one embodiment, said sub-audible signal is originating from the area of the lower esophageal sphincter of a subject. In one embodiment, said sensor comprises a plurality of sensors. In one embodiment, said system further comprises a device for converting the sub-audible signal into a digital signal, wherein said sub-audible signal is captured by said sensor in electrical communication with said device. In one embodiment, said device is selected from the group consisting of an analog to digital converter device. In one embodiment, said system further comprises software capable of transforming a digital signal by a conversion algorithm selected from the group consisting of a fast Fourier Transform (FFT) and Continuous Wavelet Transform (CWT), wherein said software is in operable combination with a computer processor. In one embodiment, said system further comprises software capable of capturing a variable selected from the group consisting of frequency, range, amplitude, and duration in time, wherein said software is in operable combination with a computer processor. In one embodiment, said system further comprises software capable of visually displaying a signal in a graphical output comprising amplitude, time, and frequency, wherein said software is in operable combination with a computer processor. In one embodiment, said system further comprises software capable of distinguishing a reflux event from a non-reflux event, wherein said software is in operable combination with a computer processor.

In one embodiment, the present invention provides a method, comprising, a) providing, i) a subject, and ii) a system comprising a low frequency sensor in electronic communication with an analog-to-digital signal converter device, wherein said sensor is capable of capturing a sub-audible signal; and b) attaching the sensor externally to said subject, and c) capturing a sub-audible signal with said sensor of an esophageal movement of said subject, d) communicating said signal to said analog-to-digital signal converter device. In one embodiment, said method further provides a computer processor capable of analyzing said digital signal and comprising: step e) analyzing and graphically viewing said sub-audible signal. In one embodiment, said sensor is a very low frequency sensor. In one embodiment, said method comprises a plurality of very low frequency sensors. In one embodiment, said sensor is an accelerometer. In one embodiment, said system does not include an analog recording device. In one embodiment, said sub-audible signal ranges in frequency between 0.1 and 40 Hertz. In one embodiment, said subject is selected from the group comprising a pre-term infant, an infant, a child, a teenager, and an adult. In one embodiment, said subject is at risk for a gastroesophageal reflux disease. In one embodiment, said esophageal movement is in the area of the lower esophageal sphincter. In one embodiment, said capturing a sub-audible signal is selected from the group consisting of an acidic and a non-acidic condition of said subject. In one embodiment, said signal is further analyzed by variables selected from the group consisting of frequency range, amplitude, and duration in time. In one embodiment, said attached sensor is located on the exterior of said subject's body in locations selected from the group consisting of the anterior thoracic cage between the sub-xiphoid process and the thoracic inlet and the posterior thorax over the esophageal area. In one embodiment, said method further comprises software capable of distinguishing a reflux associated event from a non-reflux associated event and using said software for distinguishing a reflux associated event from a non-reflux associated event.

In one embodiment, the present invention provides a method, comprising, a) providing, i) a subject having a reflux movement; ii) a system comprising a low frequency sensor in electronic communication with an analog-to-digital signal converter device, wherein said sensor is capable of capturing a sub-audible signal; and b) attaching the sensor externally to said subject, and c) capturing a sub-audible signal with said sensor of an esophageal movement of said subject, d) communicating said signal to said analog-to-digital signal converter device. In one embodiment, said further provides a computer processor capable of analyzing said digital signal and comprising: step e) analyzing and graphically viewing said sub-audible signal.

In another embodiment, the present invention contemplates a method, comprising, a) providing, i) an externally attached very low frequency sensor, wherein said sensor is capable of capturing a sub-audible signal, wherein said system does not include an analog recording device, ii) a subject, wherein said subject has an esophageal movement, wherein said esophageal movement comprises an upward movement, b) capturing a sub-audible signal from an esophageal movement in a subject, and c) graphically viewing said sub-audible signal. In one embodiment, the low frequency sensor is an accelerometer capable of capturing a signal ranging between 0 and 100 Hertz. In one embodiment, the low frequency sensor is an accelerometer capable of capturing an acoustical signal below 60 Hertz and above 0 Hertz. In a preferred embodiment, the low frequency sensor is an accelerometer capable of capturing a signal below 40 Hertz and above 0 Hertz. In one embodiment, the sub-audible signal ranges in frequency between 0.1 and 40 Hertz. In one embodiment, the sub-audible signal is a signal originating at the lower esophageal sphincter of a subject. In one embodiment, the subject is selected from the group comprising a pre-term infant, an infant, a child, a teenager, and an adult. In one embodiment, the sub-audible signal is captured from an event associated with an acidic condition of a subject. In one embodiment, the sub-audible signal is captured from an event associated with a non-acidic condition of the subject. In one embodiment, the signal is further analyzed by variables selected from the group consisting of frequency range, amplitude, and duration in time. In one embodiment, the sensor is attached by any means for keeping the sensor in place. In one embodiment, sensor is attached by means including but not limited to touch, tape, glue, tension device, and the like. In a preferred embodiment, the attached sensor is located on the exterior of a subject's body. In one embodiment, the locations include but are not limited to the anterior thoracic cage between the sub-xiphoid process and the thoracic inlet, the posterior thorax over the esophageal area, and the like. In one embodiment, the method further comprises software capable of distinguishing a reflux associated event from a non-reflux associated event. In one embodiment, the method further comprises software capable of real time data analysis. In one embodiment, the method further comprises software capable of analyzing said sub-audible signal for distinguishing a reflux associated event from a non-reflux associated event and using said software to distinguish a reflux associated event from a non-reflux associated event.

DEFINITIONS

To facilitate an understanding of the present invention, a number of terms and phrases are defined below:

The use of the article "a" or "an" or "the" is intended to include one or more. For example, as used in this application, the singular form "a," "an," and "the" include plural references unless the context clearly dictates otherwise. For example, the term "a sensor" includes a plurality of sensors, including several types of sensors.

As used herein, a "subject" refers to any animal, such as humans, including those with and without a disease symptom, and further comprises an animal of any age, including a pre-term infant, an infant, a child, a teenager, and an adult. Generally, the terms patient and subject are used interchangeably, unless indicated otherwise herein.

As used herein, the term "patient" refers to any animal (for example, a warm blooded mammal) comprising humans and non-human animals, where non-human animals include but are not limited to non-human primates, mice, rodents, farm animals (for example, cattle, horses, pigs, goats, and sheep), pets (for example, dogs, cats, ferrets, and rodents) and the like, for example, an individual to be diagnosed, treated (e.g., administered an anti-reflux therapy) or monitored using the compositions and methods of the present invention, such as a test for upward esophageal movement in an individual with GERD. A patient "having" a disease or condition, such as reflux, is a patient diagnosed with a disease, such as a "patient having a reflux disease."

As used herein, the term "individual" refers to any subject as described herein that may or may not be a patient.

As used herein, the term "gastroesophageal" or "gastroesophageal" refers collectively to the stomach, esophagus, and the connecting lower esophageal sphincter (LES).

As used herein, the term "stomach" refers to a sac between the esophagus and the small intestine.

As used herein, the term "esophagus" refers to a muscular tube that extends from the neck to the abdomen and connects the back of the throat to the stomach, allowing downward motion of food traveling from the mouth to the stomach, and conversely allowing upward motion of stomach contents which may or may not reach the mouth.

As used herein, the term "lower esophageal sphincter" or "LES" refers to a circular smooth muscle at the lower end of the esophagus, located where the esophagus meets the stomach, generally acting like a valve for allowing food in while keeping stomach contents out of the esophagus and airway, however sometimes allowing the backflow of stomach contents into the esophagus and airway.

As used herein, the term "gastroesophageal" or "gastroesophageal" in reference to reflux refers to an upward movement, i.e. reflux, of stomach contents back up into the esophagus.

As used herein, the term "gastroesophageal reflux" or "GER" or "gastric reflux" or "reflux" refers to when the lower esophageal sphincter (LES) opens spontaneously, for varying periods of time, or does not close properly resulting in stomach contents rising up into the esophagus, for example a cause of "heartburn," in adults, "colitis," vomiting (regurgitation)," burp, etc. In other words, "gastroesophageal reflux" or "reflux" refers to stomach contents regurgitating or moving up (refluxing) into the esophagus. This movement of stomach material is through the area of the LES into the esophagus.

As used herein, the term "heartburn" refers to a burning sensation generally below the breastbone that occurs after eating or at night that is a symptom of GER but may or may not be a result of gastroesophageal reflux disease (GERD).

As used herein, the term "gastric refluxate" or "refluxate" in reference to stomach contents refers to materials, such as fluids, solids, gas bubbles, and the like, moving through the area of the LES into the esophagus.

As used herein, the term "Gastroesophageal reflux disease" or "GERD" refers to a more serious form of gastroesophageal reflux (GER) associated by factors including a malfunctioning LES, obesity, slow stomach emptying, weak muscular contractions in the esophagus, exercise, pregnancy, smoking, certain hormones, many foods, and some medications, which results in a chronic condition often comprising injury to the lining of the esophagus.

As used herein, the term "acoustic GERDometer" or "GERDometer" or "GERD-o-Meter" refers to a non-invasive method of assessing both acid GER and non-acid GER events in relation to diagnosing a disease and analyzing efficacy of treating that disease.

As used herein, the term "event" in reference to a gastroesophageal event, refers to a motion of gastroesophagus resulting in an upward or downward motion of fluids and food. In general, a "downward gastroesophageal event" refers to swallowing while an "upward gastroesophageal event" refers to a reflux associated event or "GER." In reference to "identifying a reflux event" or "signal associated with a reflux event" or "reflux event" or "associated reflux event" refers collectively to a data set comprising a low frequency signal associated with a reflux event or "GER," see, for example, FIGS. 5A and 5B, and FIG. 7C. Additionally, a GER also refers to low frequency sounds and acoustic signals associated with the movement of fluid between the stomach and esophagus, including but not limited to movements of the LES, such as opening and closing, esophageal movements, such as peristaltic movements of muscles, stomach muscle contractions, etc.

As used herein, the term "identifying" in reference to an esophageal movement refers to the process of analyzing a captured physiological motion, for example, a movie of ultrasound images during a GER event, such as a reflux movement, a burp etc., for comparison to and categorizing it as an esophageal movement. For example, identifying a reflux event refers to captured signals in a very low frequency range which upon analysis show at least one peak with energy levels above background, see, for example, FIGS. 5A and 5B, and FIG. 7C.

As used herein, the term "frequency" in general refers to a measurement of how often an event, such as a motion of the esophagus, occurs. "Frequency" in relation to a captured signal of the present invention refers to a measurement in units of Hertz.

As used herein, the term "very low frequency" or "VLF" refers to frequencies ranging from 0 Hz-40 kHz while in general, the term "low frequency" or "LF" refers to frequencies ranging from 40 kHz-300 kHz. In reference to a sensor, any sensor capable of capturing accurate signals in the very low frequency range may be referred to as a VLF or LF.

As used herein, the term "medium frequency" or "MF" refers to frequencies ranging from 300 kHz to 3000 kHz.

As used herein, the term "high frequency" or "HF" refers to frequencies ranging from 3000 kHz (3 MHz)-300 MHz.

As used herein, the term "very low frequency sensor" refers to a sensor capable of capturing a signal that converts into an electromagnetic wave in the range of 0 Hz-40 kHz. In particular, a very low frequency sensor of the present invention provides a "reliable" or "accurate" signal from a low frequency range, as apposed to a sensor capable of capturing low frequency signals which are distorted in some way, such as a sensor calibrated for signal capture at high frequencies such that the low frequency range is distorted.

As used herein, the term "sensor" refers to a device for providing a measurement of the total specific force of a sound wave on the sensor (such that F (force)=mass (m) times acceleration (a)) in proportion to acceleration in Hz units, for example, a sensor such as a low frequency sensor, i.e. an accelerometer and the like.

As used herein, the term "hertz" or "Hz" refers to a unit of measurement indicating the number of cycles per second a sound wave is being transmitted. Generally this measurement is listed in Hz, kHz (kilohertz or 1,000 Hertz), MHz (megahertz or 1 million Hertz) and GHz (gigahertz or 1 billion Hertz).

As used herein, the term "sub-audible" in reference to an electromagnetic signal or sound wave, refers to a signal below 0 decibels (db), i.e., below the range of usual human hearing or for example, low frequency signals in the range of 1 Hz to 40 Hz (and in some cases including signals below 300 Hz), in which case the db level is slightly greater than 0. In contrast to "audible" Which refers to sound waves in a human speech frequency range that the majority of humans easily heat from 300 Hz to 3000 Hz, depending on the decibel level of the waves.

As used herein, the term "acoustic wave" or "sound wave" refers to a mechanical wave that may be converted into a proportional "electromagnetic signal."

As used herein, the term "accelerometer" refers to a device for detecting a sound wave, such as an acoustical signal, and providing an electrical signal representative of such waves as a measurement, such as a measure of sound wave, a measure of a vibration, a measure of a motion, a measure of a physiological motion, and the like. Typically, an accelerometer comprises a transducer for converting an acoustic signal into an electromagnetic signal. In some embodiments, a transducer is connected to the accelerometer.

As used herein, the term "signal" refers to a varying quantity that can carry information, such as a sound wave, an acoustic signal, an electromagnetic signal, such as an electromagnetic signal produced by an accelerometer in response to detecting a "very low frequency acoustic signal" or "very low frequency signal".

As used herein, the term "signal processing" refers to a field of techniques used to extract information from signals.

As used herein, the term "digital stop band" or "digital stopband" in reference to a filter, refers to an algorithm for eliminating certain frequencies, such as a band of frequencies, or signal at a particular frequency, for example, a digital stop band filter described in U.S. Pat. No. 5,876,350, herein incorporated by reference, such that a digital stop band filter is capable of removing a background 50 or 60 Hz "hum." A "hum" refers to background electronic noise produced by a power supply, such as an "electric hum" produced by an audible oscillation frequency of the mains alternating current or nearby electronic equipment.

As used herein, the term "band-stop" in reference to a filter refers to attenuating frequencies within a specified band, i.e. the "stop-band", while allowing frequencies above and below the stop-band to pass through. In some applications the filter is a physical filter, in other applications the filter is a digital filter.

As used herein, the term "band-stop filter" also refers to a "band-reject" or "band-rejection" or "band-elimination" or "notch" filter. A "band-stop filter" may comprise several filters in parallel or in series, for example, a band stop filter for low frequencies may comprise a low-band pass and a high-band pass filter, wherein the low pass frequencies are collected for further analysis.

As used herein, the term "notch" in reference to a frequency refers to a frequency of maximum attenuation.

As used herein, the term "bandpass" or "band pass" in reference to a filter refers to a filter that passes frequencies in a desired range and attenuates frequencies outside that range.

As used herein, the term "low-pass" in reference to a filter refers to a filter that passes low frequencies and attenuates high frequencies in contrast to a "high-pass" filter that passes higher frequencies and attenuates lower frequencies.

As used herein, the term "software capable of transforming a time signal by a conversion algorithm" refers to software comprising conversion algorithms such as a fast Fourier Transform (FFT) and a Continuous Wavelet Transform (CWT).

As used herein, the term "Fast Fourier Transform" or "EFT" refers to a conversion algorithm for computing a discrete Fourier transform (DFT) and its inverse, for example, a prime factor algorithm (PFA) (Good-Thomas FFT algorithm), such as a Cooley-Tukey Prime-Factor FFT, a Bruun's FFT algorithm, a Rader's FFT algorithm, and Bluestein's FFT algorithm, and the like, where a "Fourier transform" also refers to the frequency domain representation of a function and the process/formula that "transforms" one function into the other, where the transform is usually given a more specific name depending upon the domain and other properties of the function being transformed.

As used herein, the term "Discrete Fourier Transform" or "DFT" refers to a mathematical transformation, regardless of how it is computed, while "FFT" refers to any one of several specific algorithms for the DFT.

As used herein, the term "Fourier analysis" refers to an algorithm for transforming one function into another, which is also called a "frequency domain representation" or simply the "DFT" of the original function (which is often a function in the time domain).

As used herein, the term "Contiimous Wavelet Transform" or "CWT" refers to an algorithm for decomposing a signal hlto wavelets, where such "wavelets" are small oscillations that are highly localized in time. The CWT is used to construct a time-frequency representation of a signal that offers very good time and frequency localization (amara.com/current/wavelet.html; Christopher Torrence and Gilbert Compo, "A Practical Guide to Wavelet Analysis", Bulletin of the American Meteorological Society, v. 79, no. I, p. 61-78. January 1998; //paos.colorado.edu/research/wavelets/; all of which are herein incorporated by reference. Examples of CWT capable software packages include but are not limited to AutoSignal™ Systat Software, Inc., San Jose, Calif., USA and a FORTRAN based public domain CWT wavelet analysis package WAVEPACK found at //paos.colorado.edu/research/wavelets/.

As used herein, the term "software capable of capturing a variable" refers to software comprising a program for isolating a variable, such as a variable isolated from a captured signal or from input information.

As used herein, the term "variable" refers to a symbol or name that represents a value, where variables can be quantitative, such as a frequency range, amplitude, and duration in time, or qualitative, such as variables coded to appear numeric but their numbers are numerically meaningless, as in male=1, female=2. Further, some variables are manipulated by the experimenter, such as choosing categories of age, gender, etc. of a subject, and others are measured from the subjects, such as a gastroesophageal movement. The former variables are called "independent variables" or "independent measures" whereas the latter are called "dependent variables" or "dependent measures."

As used herein, the term "system" refers to a combination comprising people, devices, and methods organized to accomplish a set of specific functions, including but not limited to personnel, procedures, materials, tools, equipment, facilities, and software. Elements of this composite entity are used together in the intended operational or support environment to perform a given task or achieve a specific purpose, support, or mission requirement, such as a diagnostic test for GERD.

In some embodiments of the system, certain elements are in electronic communication with other elements thereby being "in operable combination." "Electronic communication" can be implemented in a hard-wired electrical connection, e.g., wires, a shielded cable, or an optical connection, e.g., an optical fiber, or a wireless communication, e.g., infrared or radiowaves, or a combination thereof, and the like.

As used herein, the term "analog-to-digital signal converter" or "A/D signal converter" or "ADC signal converter" refers to an electronic device that converts an input analog voltage (or current) to a digital number.

As used herein, the term "childbirth" or "labor" or "birth" or "partus" or "parturition" refers to the culmination of a "pregnancy" or "gestation period" with the delivery, including vaginal and cesarean section, of one or more newborn infants from a female's uterus.

As used herein, the term "gestation period" refers to an average time the embryo spends inside the female, therefore the actual time for an individual within a species may be less than or greater than the average for that species. As used herein, an exemplary gestation used herein is in reference to a human, refers to approximately 37-41 weeks, however gestation in reference to other animals is a different time period, for example, a dog's gestation period is 63 days, a cat's gestation period is 63-69 days, an elephant's gestation period is 22 months, et cetera.

As used herein, the term "premature infant" or "premature" or "preterm" or "preemie" refers to a human subject born before 37 weeks of estimated gestational age.

As used herein, the term "very preterm" refers to a human subject of <30 weeks' gestation.

As used herein, the term "early preterm" refers to a human subject ranging in age from 23-27 weeks gestation and an infant delivered prior to 27 weeks gestation.

As used herein, the term "developing preterm" refers to a human subject ranging in age from 28-32 weeks gestation.

As used herein, the term "preterm labor" refers to labor in a human subject before 37 weeks of gestation.

As used herein, the term "ex-premie" or "ex-preterm" refers to a human subject that was born before 37 weeks of gestation.

As used herein, the term "post term" refers to a human subject born after 42 weeks gestation.

As used herein, the term "newborn" refers to a human subject ranging from birth to four weeks of age.

As used herein, the term "infant" refers to a human subject ranging in age from 0-12 months of age.

As used herein, the term "full-term" refers to a length of time for a human pregnancy that ranges from 37 to 42 weeks gestation, this time period is specific for each type of animal.

As used herein, the term "chronologic" or "birth age" refers to time that has elapsed since birth.

As used herein, the term "gestational age" refers to an estimated time since conception.

As used herein, the term "corrected age" refers to the age of a human subject corrected for prematurity.

As used herein, the term "children" refers to a human subject ranging from 12 months to 12 years in age.

As used herein, the term "adolescent" or "teenager" or "teen" or "youth" or "young adult" or "lighty" or "youngster" or "youngin" or "shorty" or "young person" or "emerging adult" refers to a human subject ranging from 13-19 years of age. As used herein, The World Health Organization (WHO) defines adolescence as the period of life between 10 and 19 years of age (Goodburn, Elizabeth A., and Ross, David A. (1995). "A Picture of Health: A Review and Annotated Bibliography of the Health of Young People in Developing Countries." Published by the World Health Organization and UNICEF). In contrast, in the United States, adolescence is generally considered to begin somewhere between ages 12 and 14, and end between ages 19 to 21.

As used herein, the term "adult" refers to a human subject of greater than 19 years in age.

DETAILED DESCRIPTION OF THE INVENTION

Figure 1A:
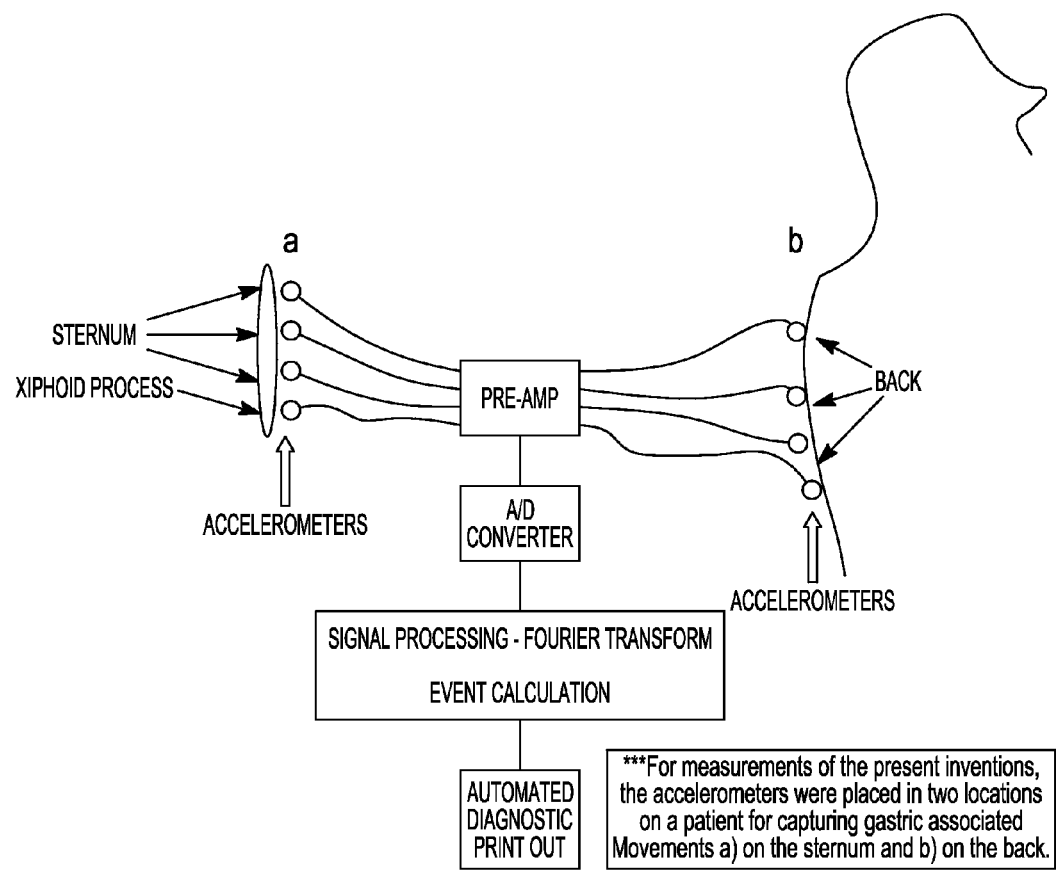
FIG. 1A) shows exemplary arrays and locations of one, two, three and four miniature accelerometers as very low frequency sensors placed on the skin a) to the left of a patient's xiphoid process and advancing up the sternum and b) on the back (posterior thorax), that captured sub-audible signals of the present inventions originating at the lower esophageal sphincter area and B) shows an exemplary system of the present invention in electronic communication [8], [1] a low frequency accelerometer, [2] a preamplifier, [3] a step amplifier, [4] a recorder amplifier, [5] an analog to digital capture recorder with data storage, [6] a computer processor and [7] a graphical output, all in electronic communication [8]. Captured signals were processed through sufficient pre-amplification to an analog-to-digital signal converter at a sample rate of 250 samples per second and recorded.

The present invention provides compositions and methods useful in the diagnosis and management of Gastroesophageal Reflux. Specifically, the inventions provide a device and methods of using the device for accurately, quantitatively, and non-invasively diagnosing Gastroesophageal reflux disease (GERD) in both patients at risk for GERD and patients demonstrating reflux-like symptoms. In particular, the inventions relate to detecting and analyzing upward esophageal movements in patients, such as human infants, children, and adults.

Devices and methodology of the present inventions are important to neonatologists, pediatricians, internists, surgeons, developmentalists, pediatric gastroenterologists, teen gastroenterologists, adult gastroenterologists, pediatric neurologists, teen neurologists, adult neurologists, in addition to any professional caring for patients with reflux and other conditions interfering with feeding, including, but not limited to, cerebral palsy, et cetera. These inventions are contemplated for application by allergists, nutrition specialists and physical therapists/occupational feeding specialists and speech pathologists interested in non-invasive, accurate method of diagnosing GER and GERD for choosing interventive treatments and comparing the success of different therapies.

Due to the large number of patients, adults, teens, and children, who suffer from reflux in combination with the lack of accurate diagnostic tools and effective treatments, compositions and methods of the present inventions are essential for making progress in diagnosis, understanding and treating GERD in infants and adults to have a more accurate and non-invasive diagnostic modality. Thus, the use of the systems comprising accelerometric diagnostic tools described herein are contemplated to be of critical importance in establishing a rational method of diagnosing and treating acid and non-acid GERD in adults, as well.

The practice and understanding of clinical medicine is concerned with understanding and interpreting acoustic signals from bodily functions, in particular those signals or lack thereof related to dysfunction and disease. The abdominal region of the human body emits a variety of acoustic signals, including mechanical vibrations, noises, electrical currents, etc., as the underlying organs perform their normal cycle. One practice currently used by clinicians to listen the abdomen using auscultation, which involves positioning the stethoscope on the abdominal surface for listening to sounds. In one examination, bowel sounds occurred at frequencies below 100 Hz with low amplitude where the low amplitude rendered them undetectable by conventional auscultation. Further, abdominal sounds that occur below 100 Hz are also susceptible to interference from heart movement induced signals. On the other hand bowel sounds occur at a higher frequency and are believed to be a component of low frequency sound capable of being heard. In other words, measurements of low intensity, low frequency abdominal vibrations and sounds are difficult to perform accurately in part due to the interference from other organs such as heart and lungs and partly because they are below the range of human hearing and sometime below the range of auscultation. However, it was found that listening to frequencies range between 130 Hz and 280 Hz a window exists where elevated bowel sounds are not affected by interference from other organs (Hession, et al., Bioengineering In Ireland Conference, Jan. 27-28, 2006, Clybaun Hotel, Galway; herein incorporated by reference).

Moreover, several types of methods were described for detecting reflux events, see below. However none of these demonstrated the capability to accurately and non-invasively measure reflux events, particularly in infants, as in contrast to those described herein in the Examples. For example, U.S. Pat. No. 6,697,984, herein incorporated by reference, is directed at treating reflux, wherein the lower esophageal sphincter was stimulated via surgical intervention. A measured response to treatment was described as using a "sensor for sensing mechanical wave movement or electrical signals representative of high motility following swallowing." These sensors were shown attached surgically (quite an invasive procedure) inside a body. The sensing equipment was described as either a "piezo-electric type sensor for detecting mechanical movements or acceleration [or a] conventional electrode for detecting electrical signals representative of motility [or an] impedance sensor or any other available sensor for detecting esophageal movement." However there was no information provided that showed an actual reflux event was detected by this sensing equipment. Further, an external sensor, or an accelerometer or low frequency data capture or analysis was not described. In another example, U.S. Pat. No. 5,058,600; herein incorporated by reference, used an accelerometer for generating electrical signals corresponding to the physical vibration of breathing noise with a pulmonary monitor for generating a second electrical signal corresponding to a phase of the patient's breathing and an analyzer for combing these electrical signals for providing a graphical readout of an acoustical evaluation of upper airway obstruction. However this publication did not describe reflux events or process reflux data comprising a time variable or isolation of a time variable for a reflux event. Further, although an analog to digital converter was used in between the accelerometer means and the pulmonary monitor in U.S. Pat. No. 5,058,600, the publication does not disclose the use of an amplifier. Moreover, the frequency range over which measurements were collected covered 0-5,000 kHz and 0-3,000 Hz ranges, where peaks were identified between 200 Hz and 1,500 Hz, and where a sample was labeled as "glottic" if a broad peak occurred at a point less than 0.75 kHz, where an airway event was said to occur between 50 Hz and 200 Hz.

Accelerometers in general were used for many medically related applications including those described in previous publications by the inventors for capturing and recording the acoustic patterns of swallowing in infants, for example, Reynolds, Vice, Bosma, and Gewolb, Dev Med Child Neurol., 2002, 44(9):587-92 and Reynolds, Vice, and Gewolb, Dev Med Child Neurol. 2003 45(7):442-6; all of which are herein incorporated by reference. However, unlike the low frequency sampling rates, below 100 Hertz, of the present inventions, the sampling rates previously used were at least 1600 Hertz. In fact, the inventors discovered that using compositions and methods similar to those described in these publications were not capable of capturing a reflux event as described and shown in the Examples provided herein, see, specifically, Example III.

Furthermore, Lazareck, et al., (2004) IEEE Transactions on Biomedical Engineering, 51(12):2103-2112; herein incorporated by reference, used externally placed accelerometers to collect data from patients, however low frequency data was specifically eliminated as stated: "The signals were amplified with the same gain for all subjects and bandpass filtered (50-2500 Hz) in hardware to minimize very-low-frequency movement artifacts and high-frequency noises." Page 2105, paragraph C.

Furthermore, unlike currently used methods, such as the "gold standard" pH measurements, the methods of the present inventions do not rely on monitoring internal pH changes over relatively short time periods, such as a few minutes to a few hours of pH measurements (as shown in tracings). Moreover, sensors of the present inventions can remain in place for hours to days, providing a clearer and more accurate picture of a symptom complex, such as reflux disease, than prior methods. These advantages are especially important in diagnosing GERD in newborn infants and patients of any age with cerebral palsy where movements specific to either the gastroesophageal or gastrointestinal system are difficult to distinguish from other types of physiological events.

The inventions described herein relate to areas of diagnostic, accelerometric, and very low frequency detecting devices that are used for assessing acoustic waveforms of biological processes. Thus, in one embodiment, the inventions provide diagnostic devices for detecting an upward gastroesophageal movement. In one embodiment, the inventions comprise a low frequency sensor. In preferred embodiment, the inventions comprise a very low frequency sensor. Even further, the inventions comprise a very-low frequency accelerometric sensor.

I. Systems of the Present Inventions.

Figure 1B:
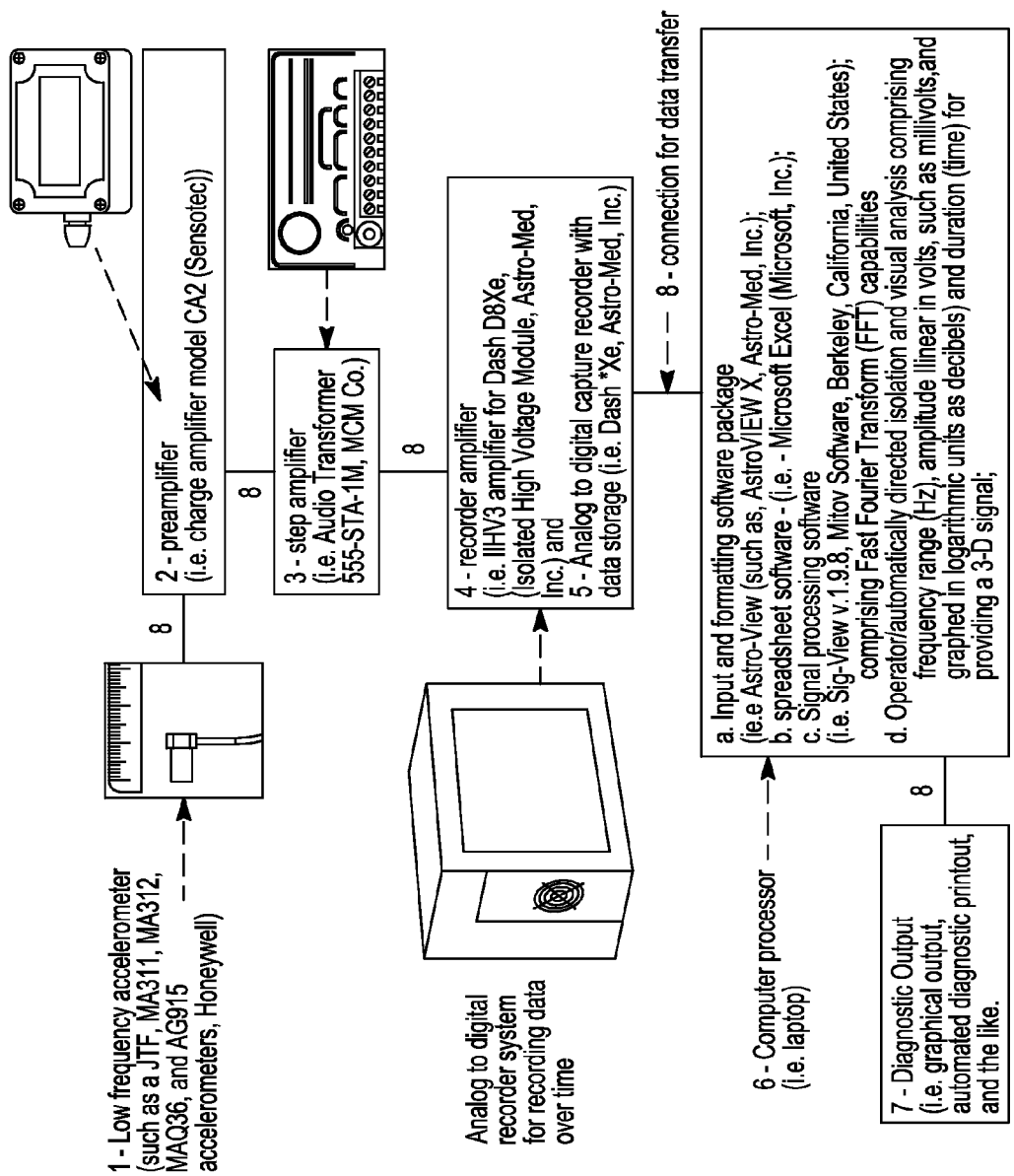

Specifically, the inventions provide exemplary systems (shown as diagrams in FIGS. 1A and 1B) in operable combination (i.e. sensors, devices and computers in electrical communication) such that the elements in FIG. 1B are connected [8], for example, by electrical wires, computer cables, wireless sending devices, wireless receiving devices, external storage devices, such as a USB flash drive, flash memory, etc., such that the connections provide a system capable of measuring a reflux event. Further, methods comprising systems of the present inventions are used for obtaining (detecting) low frequency motions for quantification and accurate diagnosis of gastroesophageal reflux events over time. Unlike current diagnostic methods these methods accomplish diagnostic and contemplated treatment goals in a non-invasive manner. The noninvasive manner is due to locating, generally by attaching, the sensor [1] on the outside of a subject [see, FIG. 1Aa], such that the sensor is an externally located sensor. Specifically, an exemplary system of the present invention for processing low frequency signals comprises, in operable order as shown in FIG. 1B, a sensor [1], such as a low frequency accelerometer for capturing a sub-audible signal, connected to a preamplifier [2] that is connected to a step amplifier [3] for amplifying the analog signal prior to entering a digital recording system comprising a recorder amplifier [4] connected to a analog to digital capture recorder with data storage [5] for storing extended recordings over time. The analog to digital capture recorder [5] is connected to a computer processor [6], such as a laptop, desktop, handheld device, and the like. A computer processor comprises software, including but not limited to an Input and formatting software package [6a], spreadsheet software [6b], signal processing software [6c], visualization software for a visual graphical output [6d], such as a 2D, 3D graph, including operator guided output and automatic (programmed) output. In one embodiment, visual output comprises frequency range (Hz) vs. amplitude (linear in volts, such as millivolts), amplitude (linear in volts, such as millivolts, and graphed in logarithmic units as decibels) and duration (time) for providing a 3-D signal. Further contemplated is a diagnostic output [7] providing information of a reflux event, such as real-time notification of a reflux event in a patient, an analysis of reflux events over time for diagnosing GERD, for diagnosing other reflux related disorders and disease, for evaluating treatments for reducing reflux events, including response to treatments for reducing GERD and other reflux related disorders.

A diagnostic output is contemplated as an automated diagnostic printout, a wireless transmission to a Personal Digital Assistants (PDA), such as a medical handheld computer, a MedicalPocket PC™, a handheld device, for example, a Handspring™, a Palm Pilot™, a smart phone, and the like), a transmission to a central computerized database, et cetera. Additionally, the diagnostic output may be specifically directed to point-of-care, such as hospital, doctor's office, home care and the like, a nursing station, a physician's office, a hospital mainframe, and the like.

In further embodiments, the inventions comprise a software package capable of analyzing digital signals. In some embodiments, the inventions provide comprise a software package capable of transforming digital signals into graphical representations. In some embodiments, the inventions provide a software package capable of graphically displaying digital signals.

Examples of very low frequency sensors and methods for detecting very low frequency acoustic signals are described in U.S. Pat. No. 6,416,483; herein incorporated by reference, which disclosed a sensor and method for detecting very low frequency acoustic signals. The sensor is capable of detecting low frequency acoustic signals in the frequency range of one-tenth Hertz to thirty Hertz, U.S. Pat. No. 7,066,894, and an International application WO/2001/072218; all of which are herein incorporated by reference.

In some embodiments, the inventions provide software capable of identifying an upward gastroesophageal event. In some embodiments, the inventions provide software capable of identifying an upward gastroesophageal event related to a disease, such as GER, cerebral palsy, and any disease associated with an upward gastroesophageal event. In some embodiments, the inventions provide software capable of identifying a reflux event. In some embodiments, the inventions provide software capable of distinguishing a reflux event from a nonreflux event. In some embodiments, the inventions provide software capable of distinguishing a reflux disease event from a nondisease reflux event.

Described herein, are systems for accurately, quantitatively, and non-invasively diagnosing gastro-esophageal reflux (GER) in patients with reflux-related symptoms. These systems comprise a very low frequency sensor device, such as an accelerometer, for detecting low frequency signals when placed externally on the skin of the patient in either the anterior thoracic cage between the sub-xiphoid process and the thoracic inlet or on the posterior thorax over the esophageal area. In some embodiments the sensors were attached using an adhesive, in other embodiments the sensors were attached using a tension device (see, FIG. 1).

The captured signals were recorded digitally, processed using signal processing algorithms, such as Fast Fourier Transform (FFT), then further analyzed for isolated variables such as frequency range (Hz), amplitude (linear in volts, such as millivolts, or in logarithmic units called decibels) and duration (time).

The inventors unexpectedly found very low frequency signals (below 40 Hz) to consistently correlate with reflux events, with a degree of specificity superior to currently used diagnostic tests, for example, pH probes and radiographic swallow studies.

Furthermore, the inventors' data was not based upon acidity of the refluxate (as with the pH probe) or dependent on tiny "snapshots" of time (as with radiographic studies). Key points regarding the compositions and methods of the present inventions are its non-invasiveness (unlike the insertion of a pH probe, or the radiographic exposure of a swallow study), its accuracy and quantifiability, the ability to use it both before and after alkalinizing therapeutic maneuvers and the capability for extended monitoring over time, as opposed to the compositions and methods shown in Table 1.

Thus, the proposed methodology would be accurate in both acidic and non-acidic conditions. This would also be important in assessing response to therapy in both adults and children on antacid treatment, whose pH probe studies are, by definition, falsely negative, i.e. the pH probe shows a negative (lack) of event while the system of the present invention provides a positive signal that correlates with a reflux event.

In addition, unlike imaging studies (radiographic, ultrasonographic, or scintigraphic), the proposed method is noninvasive and can be left in place for extended periods of time for an overall determination of the condition of a patient, rather than just providing a brief snap-shot and then extrapolating that bit of information to the general condition, of the patient. This small bit of information may or may not accurately reflect the general condition of the patient.

Thus, the new methodology would further allow frequent and extended monitoring both before and after various treatments, thus clarifying the therapeutic efficacy of treatments in general (there is currently woefully sparse data on efficacy of various treatments and maneuvers, especially in small babies) and in specific patients, who may respond better to one treatment than another.

II. Diagnosing Gastroesophageal Reflux Disease (GERD).

Gastroesophageal reflux (GER) occurs often as an involuntary retrograde passage of gastric contents into the esophagus and sometimes further up into the throat and mouth. However an actual diagnosis of GERD is made after observing both the sheer number of reflux events and associated symptoms. Symptoms of GERD may be classified as esophageal or extraesophageal. In an infant with recurrent vomiting or oral regurgitation symptoms of esophageal GERD include irritability, feeding difficulty, poor weight gain, sleep disturbance, etc. In the older child symptoms include chronic heartburn, epigastric abdominal pain, oral regurgitation, episodic vomiting, dysphagia, and rarely hematemesis. Heartburn and/or oral regurgitation are reported to occur in 2% of children aged 3-9 years, in 5-8% of children aged 10-17 years, and in 20% of adults.

The pathogenesis of esophageal GERD is related to the exposure of the esophagus to gastric contents, such as increased frequency of reflux and/or impaired esophageal acid clearance, volume of refluxate (contents of stomach moving up the esophagus), potency (i.e. high acidity), and height of refluxed material (how far up the esophagus the refluxate moves), defective tissue resistance, reduced esophageal capacitance, heightened esophageal sensitivity, and the like. A symptom of heartburn does not necessarily mean "esophagitis" a general term referring to any inflammation, irritation, or swelling of the esophagus. For example, a patient with heightened esophageal sensitivity may have as much or more heartburn as a patient with erosive esophagitis. Alternatively, other causes of esophagitis include infections (most commonly *candida*, herpes simplex and cytomegalovirus). Esophagitis symptoms include difficult and painful swallowing, heartburn, mouth sores feeling of something stuck in the throat, nausea and vomiting.

Extraesophageal symptoms of GERD include chronic cough, wheezing/asthma, apnea, bradycardia, chronic sore throat, hoarseness, dental erosions, and recurrent otitis/sinusitis The pathogenesis of extraesophageal GERD may include: (1) regurgitation into the oral pharynx or nasal passages causing direct caustic injury, inflammation, edema, eustachian tube dysfunction, or impaired sinus drainage; (2) microaspiration resulting in direct caustic injury, inflammation, edema, epithelial hypertrophy, laryngitis, pneumonitis, or vagal reflex-mediated cough, laryngospasm, or bronchospasm; or (3) stimulation of esophageal vagal afferent receptors resulting in reflux-mediated change in airway resistance or bronchial hyperreactivity (see, for example, review by Boyle, et al., "Gastroesophageal reflux disease in 2006: The imperfect diagnosis" Pediatr Radiol. 2006 September; 36(Suppl 2): 192-195, herein incorporated by reference).

When pH monitoring was used for obtaining diagnostic information (where the pH probe is internalized for up to 24 hours or more), a number of pH dips (below 4.0) are often observed that are not related to GER. Thus a mere drop in pH is not indicative of a GERD event or of a GERD diagnosis. For example, an exemplary number of pH dips "allowed" during a 24 hour time period before GERD is diagnosed is 22, approximately one per hour. When the number of pH dips is higher than 1 per hour then GERD is suspected and often treated.

In particular, infants and children normally reflux to some degree, manifested by recurrent vomiting or oral regurgitation. As an example, approximately 50% of normal term infants have reflux (vomiting 2 or more feeds/day) at the age of 2 months, in the first 6 months of life, 50-60% of infants vomit at least once daily, and 15-20% more than four times daily. Reflux in infancy is considered a developmental phenomenon supported by the rapid lessening in frequency of symptoms between the ages of 6 and 12 months. By 1 year of age, 5% of infants may still vomit once daily, but less than 1% will vomit in excess of four times a day. An example of developmental physiological observations for downward movements, as opposed to the upward movements observed during the development of the present inventions, was shown in Vice et al., Developmental Medicine & Child Neurology 2008, 50: 467-472, wherein feeding components, such as suck, swallow, respiration, may mature at different rates in individual infants. Other examples of developmentally associated differences in downward movements was shown in Reynolds, et al., Dysphagia (2009) 24:13-19, wherein swallow-associated signals of adults were compared to infants.

Current frequently used methods of diagnosing GER for determining GERD is from either invasive methods, i.e. pH probe or impedance monitor by tube insertion into infants, children and adults; endoscopy or externally by X-ray studies and ultrasound imaging; are not able to diagnose non-acid reflux, a common occurrence in neonates, may miss GER events and thus not allow an accurate diagnosis of GERD. Further, X-ray and other imaging studies additionally suffer from the limited time of the studies and may miss reflux events contributing to a GERD diagnosis.

Thus the inventors contemplate an embodiment comprising a system of the present inventions or "GERDometer" for use in a "global" determination of GER events over time necessary for accurate diagnosis of GERD. In another embodiment the inventors contemplate a method of quantitative analysis of GER events for diagnosing GERD. In another embodiment the inventors contemplate a method of diagnosing GERD as acid reflux. In another embodiment the inventors contemplate a method of diagnosing GERD as nonacid reflux. In one preferred embodiment, GERD is diagnosed prior to extensive esophageal damage.

The inventors contemplate that systems comprising accelerometers and the use of accelerometry as non-invasive method for assessing both acid and non-acid GER would enlarge the capability to diagnosis and treat GER related diseases. For example, because systems and methods of the present inventions identify nonacid-reflux events diagnosis and evaluations should be accurate even when patients remain on antacid medications, allowing for assessment of drug efficacy, unlike pH-based diagnostics. Thus in a further embodiment, the inventors contemplate using a system of the present inventions for determining effectiveness of GERD treatments by recording accelerometer signals before and after treatments for comparisons in relation to time, duration and in the case of medications, dosages, over time.

As part of the development of a "GERDometer" the inventors also contemplate determining establishing "normative" values for distinguishing nonGERD patients demonstrating "background" Ger events from GERD patients with disease associated or causing GER events. For example, the inventors contemplate identifying ranges or averages of GER events per unit of time for diagnosing GERD. Even further, the inventors contemplate correlating number of GER events with intensity for diagnosing GERD.

In other embodiments the inventors contemplate methods of the present inventions for analyzing GER events for diagnosing GER related diseases other than GERD. In additional embodiments, the inventors contemplate monitoring efficacy of treatments for other diseases for reducing numbers and intensity of GER events.

A "4-box" (Table 2) compared 12-min of FFT scores that surrounded a 4 minute segment comprises a pH recording. Thus the inventors further contemplate embodiments for obtaining FFT scores of time samples longer than 4 minutes for analyzing and grading accelerometric recordings. In particular, 1 hour of monitoring may not provide representative reflux information. In particular, infants may not have a reflux event until over 1 hour after feeding. In addition, multiple reflux events over time are necessary for providing information for use in diagnosing GERD. Thus, the inventors contemplate collecting sensor recordings up to 12 hours, preferably 24 hours and more preferably greater than 24 hour recordings. In particular, the inventors contemplate FFT analysis and scoring of 12 hour recordings for an output on a one page print out (for example, 8½ by 11 inches; 8½ by 14 inches, etc) or for observing on a computer screen, such as a 10 inch, 15 inch, etc., or for imaging for viewing, such as projected onto a white board. Further, the inventors contemplate additional methods for analyzing FFT accelerometric data in order to provide more in-depth information. In particular, the inventors contemplate comparing number and amplitude of signals collected from patients with GERD or GERD or GER associated diseases and patients with GER symptoms but disease symptoms in order to determine ranges of quantitative values for use in diagnosing disease, in particular for diagnosing GERD. Further, a series of accelerometers lining the outside of the esophagus are contemplated for use in determining the distance of refluxate moving up the esophagus towards the throat and mouth. Even further, such measurements are contemplated for use in determining whether refluxate reaches the throat.

The inventors further contemplate miniaturizing systems of the present inventions for providing a clip on device for monitoring reflux events over 24 hour time periods. This miniaturized device would be capable of being attached to the patient during normal daily and night activities.

In summary, the inventors contemplate the development of systems and methods of the present inventions into a new diagnostic tool for analyzing GER events in relation to diagnosing disease and subsequent treatments, such as GERD.

TABLE 1

A comparison of methods currently used for measuring reflux in infants.

| Method | Advantage | Disadvantage |
|---|---|---|
| pH probe | Gold standard for acid reflux<br>Reproducible (but requires 18-24 hr study)<br>Portability | Invasive-discomfort of probe<br>Does not detect non-acid reflux<br>Underestimates GER due to buffering capacity of formulas<br>Cannot detect GER if gastric pH > 4. Premies have pH > 4 90% of the time!<br>Need to d/c acid-reducing meds 24-48 hr prior to study<br>Premies with no signs of GER spent 4.5% of the time with pH < 40 in the distal esophagus |
| Contrast Studies<br>Fluoroscopy<br>UGI | Defines structural anatomy | Invasive<br>Yield for information on pathophysiology is poor<br>Risk of aspiration<br>Non-physiologic formula<br>Limited to events in the immediate post-cibal period<br>Not portable |
| Technetium 99m Scan (Scintigraphy) | Determines gastric emptying | Not portable<br>Poor sensitivity<br>Depends on volume and composition of feeds<br>Not standardized in premies |
| Esophageal Micro-Manometry | Defines pathophysiological mechanism of GER<br>Evaluation of esophageal clearance and peristalsis<br>Evaluation of sphincter dynamics<br>Measure of proximal extent of refluxate in the esophagus<br>Portable | Requires skilled personnel<br>Limited availability<br>Little normative data |
| Endoscopy | Documents esophagitis<br>Permits biopsy | Invasive<br>Anesthesia needed |
| Ultrasound | Non-invasive | Episodic; may miss GER |
| Acid/Litmus tests of oropharyngeal secretions | Non-invasive | Only picks up acid reflux<br>Needs to be validated |
| Multichannel intraluminal impedance | Does not require acidity | Invasive<br>Time consuming |

EXPERIMENTAL

The following examples are provided in order to demonstrate and further illustrate certain preferred embodiments and aspects of the present invention and are not to be construed as limiting the scope thereof.

Example I

Capturing a Reflux Event

The following describes exemplary compositions and methods for providing a system for capturing, measuring, analyzing and identifying a reflux event. This example describes collecting exemplary reflux events in preterm infant patients and term infant patients.

The inventors captured sub-audible signals originating in the area of the lower esophageal sphincter, i.e. a reflux event, by capturing acoustic signals from an externally placed Sensotec accelerometer model #MAQ36 (Honeywell, Inc., Columbus, Ohio) that in separate experiments was either placed on the skin of the patient's anterior thoracic cage just to the right (baby's left) of the xiphoid process (i.e., between the sub-xiphoid process and the thoracic inlet (see, FIG. 1Aa), as shown in this Example, or placed on a patient's back in subsequent experiments (see, FIG. 1Ab). The inventors substituted a posterior location due to the discovery that a stronger signal was obtained from the back sensors when compared to the sensors placed on the anterior of the patient. Alternatively, a Vibrometer #501B was used to capture similar signals.

After captured signals, with energy in the picocoulomb range, were processed through a preamplifier (Sensotec charge amplifier model CA2) and a step amplifier (Audio Transformer 555-STA-1M, MCM Co., Dayton, Ohio, United States), the captured signals were digitally recorded (using an IVH3 amplifier (AstroMed, Inc., West Warwick, R.I., United States)) into a digital capture recorder (Dash 8Xe, Astro-Med, Inc). The recorder was set up to record between three and four hours of captured data at a sample rate of 250 samples per second. For comparison, initial studies were done simultaneously with a pH Probe (Sandhill Scientific, Highlands Ranch, Colo., United States) study for providing a temporal reference for comparison with the standard procedure for detecting (acid) reflux.

Figure 2:
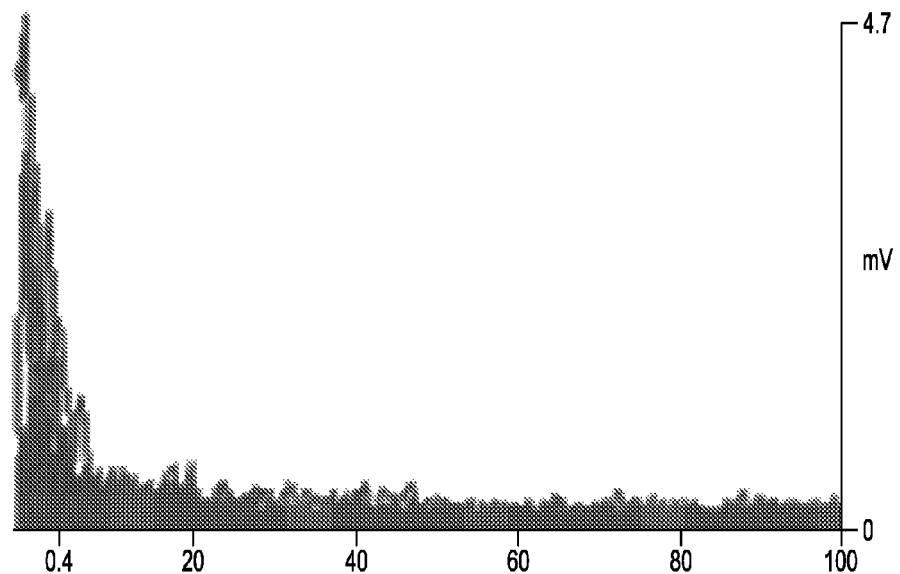
FIG. 2 shows an exemplary resulting graph of signals captured with the exemplary system shown in FIG. 1B, converted by a fast Fourier Transform (FFT) (of which a Continuous Wavelet Transform is alternatively contemplated for transformation) into a frequency domain (Hertz) shown vs. energy (amplitude) in millivolts.
Figure 5A:
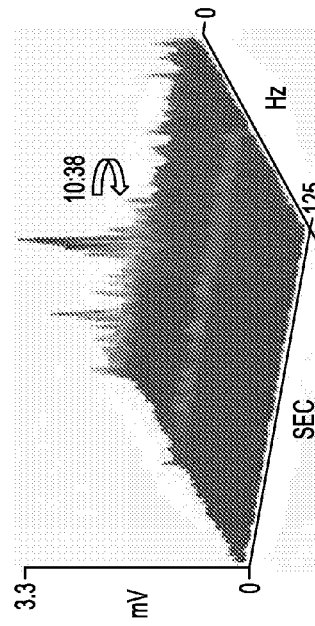
FIG. 5 shows exemplary graphs A) and B) of Fast Fourier Transformed (FFT) signals that showed non-acid associated reflux events using low frequency accelerometry measurements of the present inventions (below 40 Hz) at the same time C) the pH probe tracing was negative for any specific event by showing typical non-acidic readings with a pH of approximately 6.0. Please note the steady 60 Hz band (line) of electronic noise traversing the FFT graphs in A and B.

After completing several data sets covering sets of three and four hours of recorded data, the data was transferred into Astro-View (Astromed, Inc.) on a Dell laptop computer and then, adjusted for page-size, was further transferred to Microsoft Excel (Microsoft, Inc., Seattle, Wash., United States) from which it was imported into signal processing software (Sig-View v. 1.98, Mitov Software, Berkeley, Calif., United States). The signal processing software performed a Fast Fourier Transform (FFT), (segment length=1024 ($2^{10}$), number of segments=88, offset=679, frequency range=0.24-125.00 Hz) (see FIG. 2). Signal processing was followed by directed isolation and visual analysis for frequency range (Hz), amplitude (linear in volts, typically in millivolts, or in logarithmic units of decibels) and duration (time, seconds to minutes, over hours of duration of patient monitoring) to provide a 3-D signal (see FIG. 3). When necessary, a digital stop band filter was used to excise a 60 Hz "hum" picked up from other medical equipment in the area (see, an exemplary 60 Hz line ("hum") is shown in FIGS. 5A and B).

The majority of the significant area of interest was found below 40 Hz. Therefore, the FFT segment areas of interest below 40 Hz were processed for amplitude and duration in order to define an "event", i.e., a reflux associated movement, which was summed to calculate the number and length of events per hour over the duration of the recording study. Those areas with frequency components ≥60 Hz were interpreted as either movement artifact or non-GERD related signals and omitted from the analysis. This identification of "events" was capable of being printed out in a report as an automated diagnostic printout.

Figure 3:
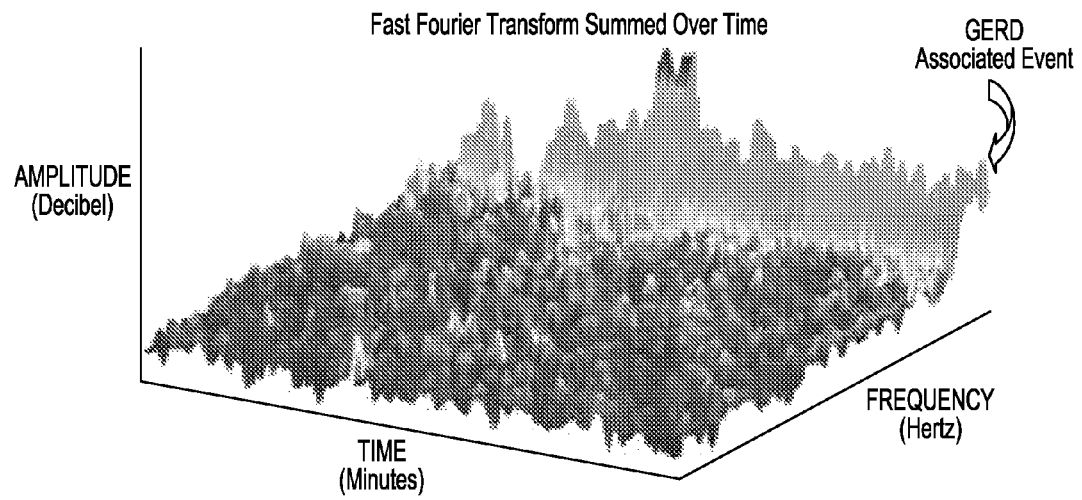
FIG. 3 shows an exemplary graph demonstrating a segment of the fast Fourier Transform (FFT) of captured signal (see, FIG. 1) in an area of interest between 0 and 40 Hertz (Hz) calculated using amplitude (up to 3.3 mV) and duration (4 minutes of time) for defining an "event", i.e., a movement associated with a reflux action, which were summed to calculate the number and length of events per hour over the duration of the recording study. Those areas with frequency components at and above 60 Hz were interpreted and negated as either movement artifact, such as a 60 Hz cycle electrical-equipment-generated interference (shown in FIG. 5), and higher frequency signals not related to GERD (see FIG. 2). This exemplary calculation of "events" was visualized and printed out in a report. Thus, the individual FFT segments were analyzed over time. This visual presentation in graph form makes the low frequency phenomenon associated with a reflux event readily observable to the interpreter.

Thus, the individual FFT segments were combined, summed, and then analyzed over time. This visual presentation of amplitude vs. Hz vs. time makes the phenomenon of a recorded "event" readily observable to the interpreter (FIG. 3). Recordings from multiple infants were visualized and compared in order to determine the parameters of a reflux associated event. In general, the inventors found that reflux events occurred as multiple signals over time, where the averaged range of reflux associated signals was at least 2-fold greater than background (see, FIG. 3). The inventors further found a range in amplitude of the signal differed between patients, such that lower energy signals were captured from some patients while higher energy signals were gathered from others. Further, the range in amplitude of reflux associated signals was also associated with the location of the sensors, such that in general the amplitude was stronger when measured with sensors on the back compared to the sensors placed on the anterior of the patient.

In conclusion, the inventors found that very low frequency signals (below 40 Hz) consistently correlated with reflux events, with a degree of specificity superior to currently used diagnostic tests, for example, pH probes and radiographic swallow studies.

Example II

The Following Example Demonstrates an Added Benefit of Using Compositions and Methods of the Present Inventions for Identifying a Reflux Event The following describes an exemplary comparison between pH probe data and accelerometric data of the present inventions. The compositions and methods of the present inventions were essentially those described in Example I. The compositions and methods of using a pH probe were standard for reflux patients, an example is provided in Pezzati, et al., Neonatology. 2007; 91(3):162-6. Epub 2006 Nov. 29 and López-Alonso, et al., Pediatrics. 2006 August; 118(2):e299-308. Epub 2006 Jul. 10; all of which are herein incorporated by reference in their entirety.

Figure 4:
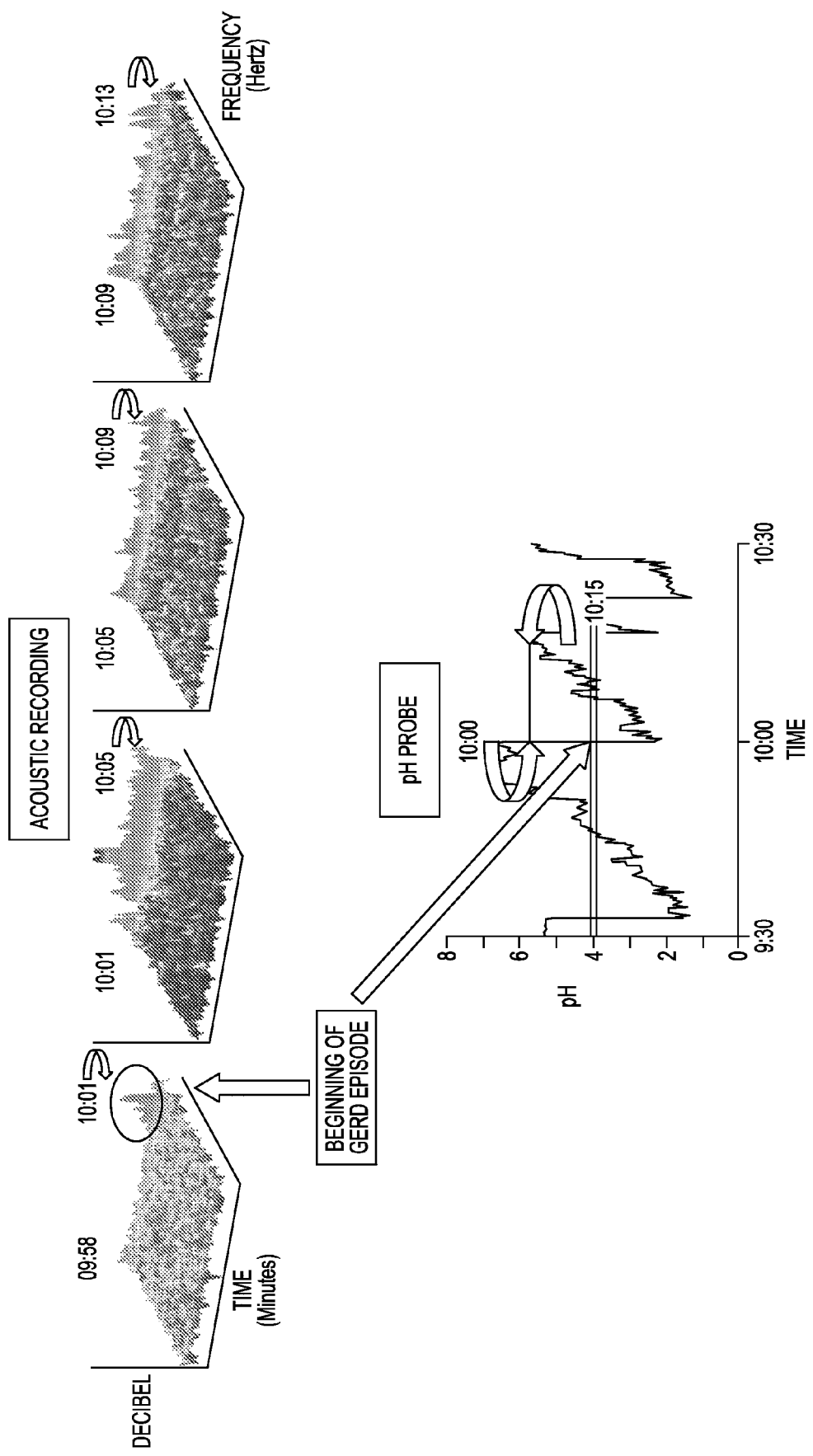
FIG. 4 shows an exemplary correlation between low frequency accelerometric data (upper area) and pH probe data (lower area). These correlations were consistent (excellent), with positive accelerometric readings, such as those shown associated with GERD in FIG. 3, occurring universally when pH probes showed an acid reflux event. No negative no peaks above background, and no signals at least 2 times above background, etc.) accelerometric recordings were obtained when pH probe readings were positive (i.e. "gold standard" pH increase/spike) for traditional diagnostic detection of acid reflux.

In particular, this comparison shows that positive accelerometric readings (an identification of a reflux event) occurred (upper area of FIG. 4) when pH probes demonstrated the "gold standard" acid reflux event (lower area of FIG. 4).

Figure 5B:
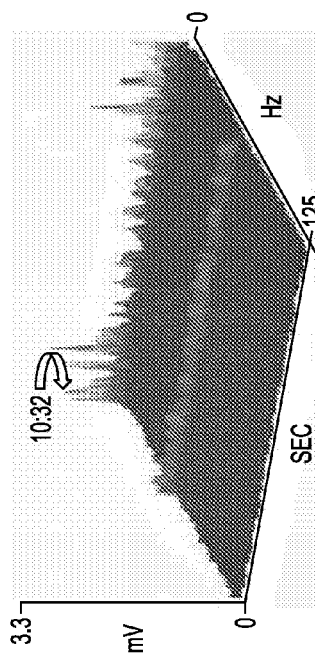
Figure 5C:
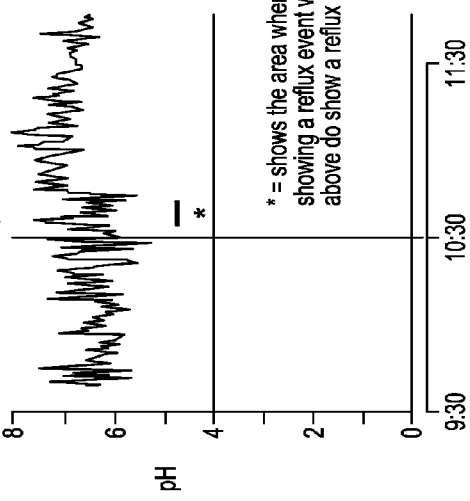

Further, another comparison (in a different patient) showed that compositions and methods of the present inventions provided a higher level of sensitivity where on several occasions the acoustic reading was "positive" while the pH probe study was "negative." (see, FIG. 5). Conversely, there were no positive pH probe events when the acoustic signal was negative. Therefore this data was contemplated to represent an acoustic recording that captured an upward non-acid reflux signal, a reflux event that is contemplated to be associated with GERD, which the pH probe missed.

Example III

This Example describes an exemplary quantitative analysis for a "GERDodometer" of the present inventions (Gewolb and Vice, poster, Pediatric Academic Societies meeting, May 2009).

In this Example, a preliminary correlative analysis was made for acid reflux and nonacid reflux events between pH and a preliminary grading system designed by the inventors. Information for this comparison was obtained from 30 ex-preterm neonates undergoing pH monitoring (internal pH probe recordings) and external monitoring using a system of the present inventions. Specifically, an accelerometer was taped to the skin over the sub-xiphoid process and/or the caudal thorax of 30 ex-preterm neonates. Signals were step-amplified to a digital recorder (sample rate 250 Hz), which captured low-frequency, sub-audible reflux-associated signals. Fast Fourier Transforms (FFTs) graphically displayed the Hz and amplitude (as described and shown herein). At least 1000 4 minute aliquots were graded and scored as described below.

This analysis focused on signals <30 Hz for a pilot scoring system devised whereby 4 min sequential (consecutive) FFT segments were graded as 0 (no signal), 1 (rare low-amplitude signal) or 2 (frequent, higher-amplitude signals) and then added together for a total grade for the 12 minute sample, i.e. the lowest grade was 0 (no captured signal during this time) while the highest grade was 6 (high signal activity). As an exemplary arbitrary grade for an initial analysis a GER total grade of 3 was chosen as a cut-off for separating a GER event (greater than and equal to 3) from a nonGER event (less than 3). The total grade was then compared to the pH measured during that time period. For an exemplary comparison, FIG. 4 shows aeries of graphs of low-frequency signals vs. amplitude in mV over time compared to a pH recording showing co-temporal acid-reflux collected as 4 minute time aliquots. Each 4-minute segment of a sample was graded visually then compared to their proximity to acid-reflux events visualized by pH monitoring. The total grade (or score) are shown as a "4-box" in the following Table 2. For this analysis, one type of GER event, acid reflux, was identified by the "gold standard" pH dip below 4.0 while a nonacid event was scored when the pH remained above 4.0. Fluids with a pH at less than 4.0 is capable of producing tissue injury outside of the stomach.

The first column, row 1, show the number of arbitrary GER events that correlated to an acid event (pH dips to 4.0 or below) as compared to the second column row 2 showing GER grades determined during 12 minute intervals where the pH remained above 4.0. This correlation was highly statistically significant (* p<0.001).

Conversely, high GER scores were found while pH monitoring showed a lack of an acid event. This finding supports the additional capability of the systems of the present inventions for identifying a non-reflux event, i.e. a GER event when the pH is above 4.0, as described herein. Thus, there was very good correlation between low GER scores and high pH recordings (negative studies or lack of a GER event) and between high GER scores and low pH recordings ("false positive" scores or the detection of an acid GER event, contemplated as captured non-acid reflux events).

However, there were a few "false negatives" (low GER scores when pH is <4). However the inventors contemplate that false negatives at this time were likely to reflect the arbitrary 4-minute segments into which the study segments are divided (i.e., the GER score depends on when the segment is divided). As a further complication of the scoring system, these events may also be reflective of the arbitrary "3" cut-off score for identifying a GER event during the 4 minute segment. Even further, this preliminary analysis may not compensate for the pH lag time when the pH does not rise in correlation with the ending of a GER event or when the rise is not immediately registered by the pH probe. Alternatively, the pH may drop and then remain low without a reflux event occurring.

Despite the fact that even this preliminary and arbitrary scoring system for 4-minute segments demonstrated a high level of accuracy, the inventors further contemplate analyzing data from a longer time segment. See, section on "Diagnosing GERD," above.

TABLE 2

Preliminary "Gerd-o-meter" comparisons where 4-minute aliquots were then graded as 0 (no signal), 1 (rare low-amplitude signal) or 2 (frequent, higher amplitude signals) and compared to their proximity to acid-reflux events visualized on pH monitoring.

| pH vs. total GER Score | pH ≤ 4 | pH > 4 |
|---|---|---|
| GER Score ≥ 3 | 69 | 441 |
| GER Score < 3 | 33 | 649* |

*p < .001

Example IV

Capturing GERD Associated Events by Digital Recordings Without the Use of an Analog Recording Device This example demonstrates the superiority of systems and methods of the present inventions over previous methods of capturing and recording physiological acoustic signals from subjects. In particular, the inventors demonstrated the capturing and processing of sub-audible signals showing both non-acidic and acidic associated reflux events.

The inventors originally contemplated that GERD events comprised primarily audible signals that would be captured by analog recording devices, such as microphones, and systems comprising microphones such as those used in previous studies for capturing burps and feeding associated esophageal movements. Further, previous publications, including published studies by the inventors, showed that analog recording of accelerometer signals captured pharyngeal events, such as swallowing for example, Reynolds, Vice, Bosma, and Gewolb, Dev Med Child Neurol., 2002, 44(9):587-92 and Reynolds, Vice, and Gewolb, Dev Med Child Neurol. 2003 45(7):442-6; all of which are herein incorporated by reference. However, the use of these previous methods did not yield the results obtained as described herein. In fact, the inventors initially used previously described systems; however, they failed to obtain the reflux associated signals as shown herein. This failure was contemplated as primarily due to the following information.

Figure 6:
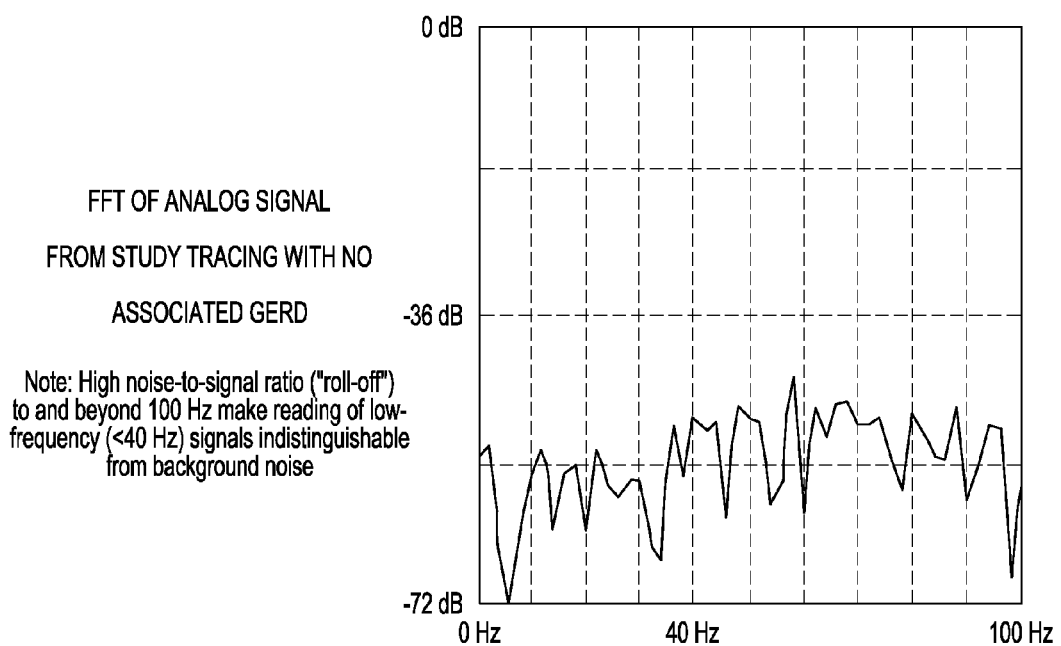
FIG. 6 shows an exemplary fast Fourier Transform (FFT) of analog signal (as opposed to digital signals of the present inventions) captured from a patient with no associated GERD, providing an exemplary study tracing where signals in the range of interest (<40 Hz reflux associated signals) are indistinguishable from the background noise. Thus this type of analog measurement would not allow the detection of a reflux associated signal.
Figure 7A:
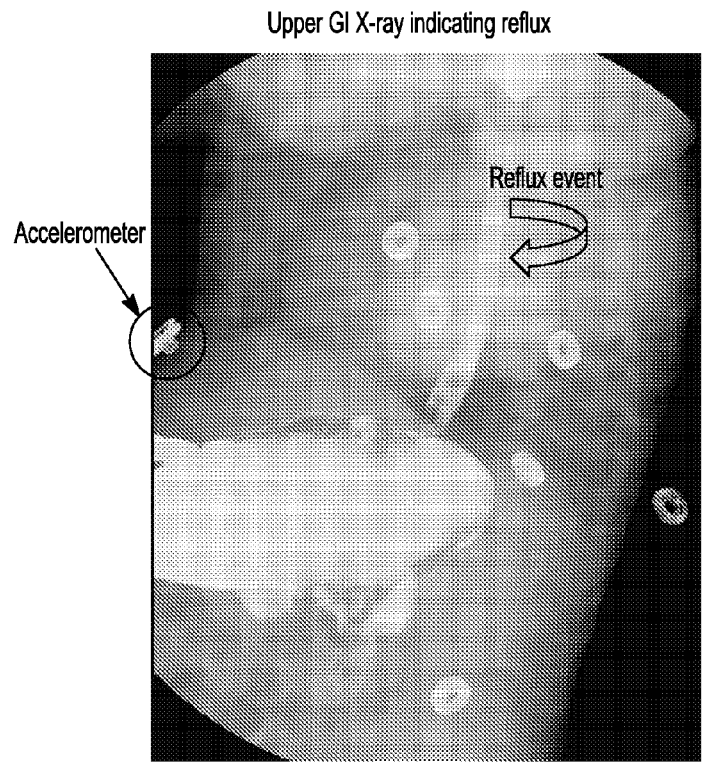
FIG. 7 shows an exemplary A) upper GI X-ray indicating reflux; B) a digital signal recording at the xiphoid occurring co-temporally with reflux event; and C) Fast Fourier Transformation (FFT) of digital signals from the tracing (FIG. 7B) at time of reflux on the upper GI (gastrointestinal) series (7A).
FIG. 7C underscores the capability of the system of the present inventions to capture sub-audible reflux signals. Specifically sounds of <40 Hz are not audible to the human ear in the decibel range represented in this Figure.
Figure 7B:
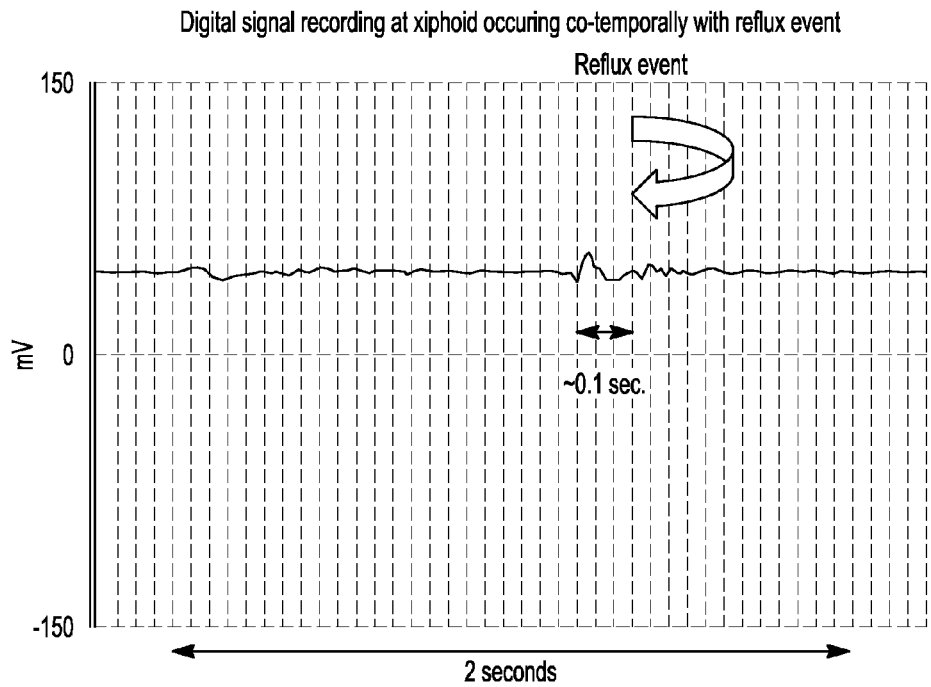
Figure 7C:
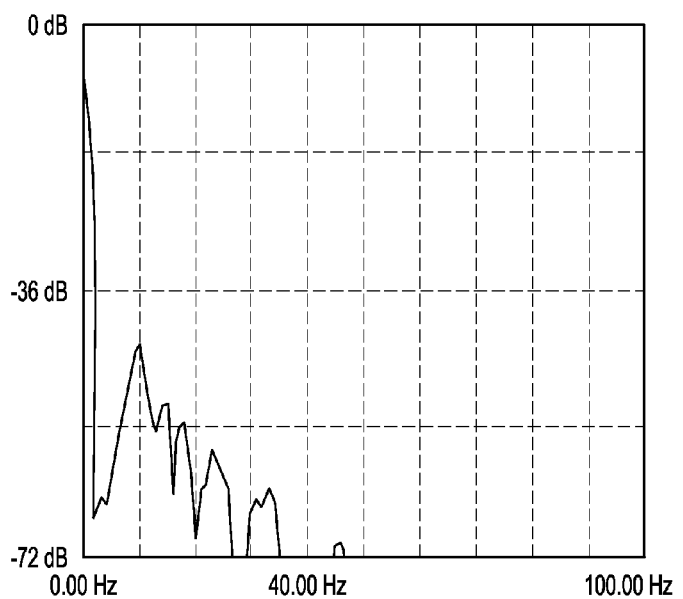

A typical case in point is that in one of the first reflux studies signals the inventors attempted to record reflux associated signals with an analog recorder, which unknowingly had masked movement at frequencies in the sub-audible range (lower than 40-60 Hz). As shown in FIG. 6, even recordings of nonGERD events showed high levels of background signal which would have masked any specific low frequency GERD associated event. In contrast, when an isolated digital recording, made at the same time an upper gastrointestinal X-ray was taken, the digital recording showed a very low frequency reflux event in parallel with the X-ray signal (FIGS. 7A-B). Therefore a specific low frequency digital signal was discovered to be associated with the reflux event. This signal was digitally isolated as shown in FIG. 7C. This digital signal, which FFT analysis revealed to have occurred at extremely low (sub-audible) frequencies (FIG. 7C), provided the surprising conclusion that at very low frequencies (<40 Hz) specific signals were marking reflux events, as described in detail herein, see Examples described above.

Example V

Capturing GERD Associated Events in Relationship to an Ultrasound Recording of Lower Esophageal Sphincter Movement This Example demonstrates the surprise of correlating an exemplary refluxate movement during a GER event with the GERD associated signal of the present inventions.

The inventors contemplated that GER associated spikes were acoustic signals caused directly by the lower esophageal sphincter valve snapping open. However, this event was contemplated as rapid event whereas the inventors' recordings of GER associated spikes lasted up to several minutes. In attempts to resolve this puzzling observation, other contemplated possibilities were that the GER signals were caused by or represented collective signals from physiological GER associated events, such as muscle contractions, including peristaltic esophageal contractions, or the actual refluxate movement. Thus the following correlative events were recorded by a simultaneous ultrasonographic study and accelerometric digital recording on an infant with GERD.

The inventors were surprised to discover that the acoustic signals correlated one on one with the tidal-like movement of the refluxate.

Figure 8A:
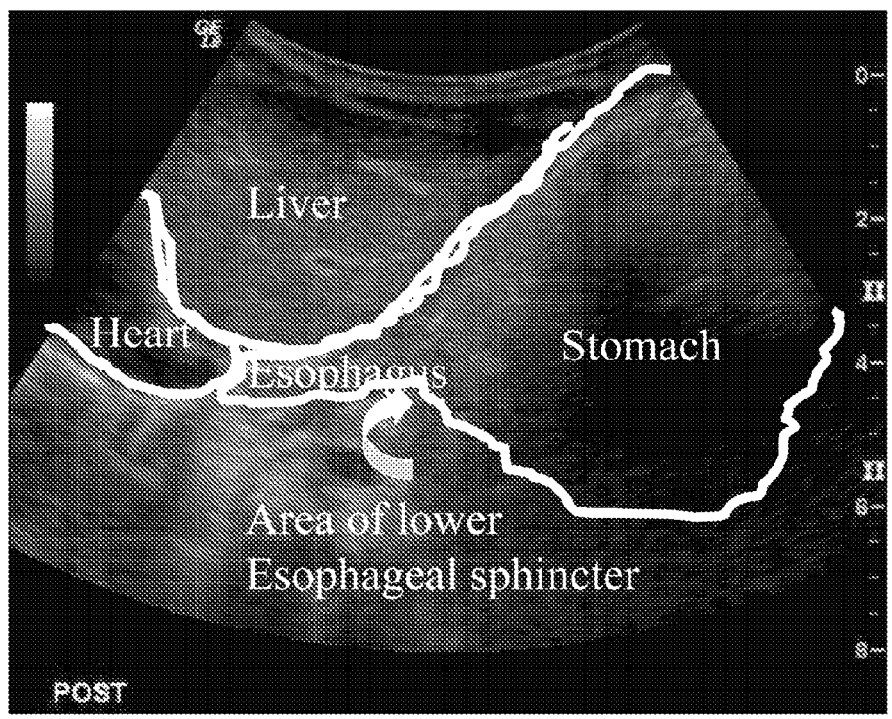
FIG. 8A shows outlines of anatomic structures labeled for ease of interpretation.
Figure 8B:
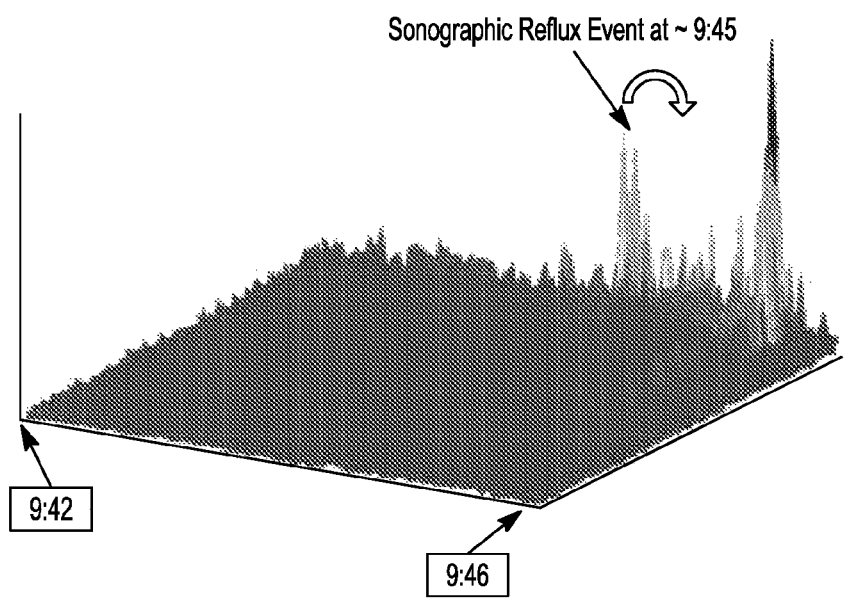
FIG. 8 shows an exemplary one on one correlation of movement in the lower esophageal sphincter recorded during a sonogram of an infant with GERD and a GER signal of the present inventions. A) shows one frame of a series of sonogram images demonstrating the movement of stomach fluid contents between the stomach and esophagus and through an area of lower esophageal sphincter as observed by the inventors in a video recording of these sonogram images, herein incorporated by reference, recorded at same time sensor recordings were made corresponding to B) the GER associated signal recorded during the reflux episode observed in the sonogram A.

A video loop was recorded from a sonogram which demonstrated movement of reflux from a stomach bubble into the esophagus (bubbles in the refluxate were observed moving in the video by the inventors), where the video is herein incorporated by reference. Since a video recording can not be shown, FIG. 8A shows a one frame of the sonogram the demonstrated the area of lower esophageal sphincter which moved during the same time as the GER associated signal was recorded in FIG. 8B. FIG. 8A was labeled in relation to other anatomic structures for ease of interpretation. FIG. 8B shows an exemplary recording obtained during the reflux episode observed in the sonogram. Taken together these data demonstrate that the accelerometric recording was sensing an actual reflux event and that the FFT analysis of that event accurately represents a GER event.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:
1. A method, comprising,
a) providing,
ii) a subject at risk of having an esophageal reflux movement;
ii) a system comprising a low frequency sensor in electronic communication with an analog-to-digital signal converter device, wherein said sensor is capable of capturing a sub-audible signal; and
b) attaching the sensor externally to said subject, and
c) capturing a sub-audible signal with said sensor of said esophageal reflux movement of said subject, and
d) communicating said signal to said analog-to-digital signal converter device.

2. The method of claim 1, further providing a computer processor capable of analyzing a digital signal from the analog-to-digital signal converter device and comprising: step e) analyzing and graphically viewing said sub-audible signal.

3. The method of claim 2, where the system further comprises software capable of transforming said digital signal by a conversion algorithm selected from the group consisting of a fast Fourier Transform (FFT) and Continuous Wavelet Transform (CWT), wherein said software is in operable combination with a computer processor.

4. The system of claim 1, further comprising software capable of capturing a variable selected from the group consisting of frequency, range, amplitude, and duration in time, wherein said software is in operable combination with a computer processor.

5. The system of claim 1, wherein the system further comprises software capable of visually displaying a signal in a graphical output comprising amplitude, time, and frequency, wherein said software is in operable combination with a computer processor.

6. The method of claim 1, wherein the system further comprises software capable of distinguishing a reflux event from a non-reflux event, wherein said method further comprises using said software for distinguishing a reflux event from a non-reflux associated event.

7. The method of claim 1, wherein the sub-audible signal ranges between 1 and 40 Hertz.

8. The method of claim 1, wherein the sub-audible signal is originating from the subject's lower esophageal sphincter.

9. The method of claim 1, wherein said sensor comprises a plurality of sensors.

10. The method of claim 1, wherein said sensor is an accelerometer.

11. The method of claim 1, wherein said system does not include an analog recording device.

12. The method of claim 1, wherein said subject is selected from the group comprising a pre-term infant, an infant, a child, a teenager, and an adult.

13. The method of claim 1, wherein said subject is at risk for a gastroesophageal reflux disease.

14. The method of claim 1, wherein said capturing a sub-audible signal is selected from the group consisting capturing of a signal of an acidic condition of said subject and capturing a signal of a non-acidic condition of said subject.

15. The method of claim 1, wherein said sensor is attached on said subject's body exterior in locations selected from the group consisting of the anterior thoracic cage between the sub-xiphoid process and the thoracic inlet and the posterior thorax over the esophageal area.

* * * * *

UNITED STATES PATENT AND TRADEMARK OFFICE
CERTIFICATE OF CORRECTION

| | | |
|---|---|---|
| PATENT NO. | : 8,568,336 B2 | Page 1 of 1 |
| APPLICATION NO. | : 13/003986 | |
| DATED | : October 29, 2013 | |
| INVENTOR(S) | : Gewolb et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twelfth Day of May, 2015

Michelle K. Lee
*Director of the United States Patent and Trademark Office*